Figure 1:
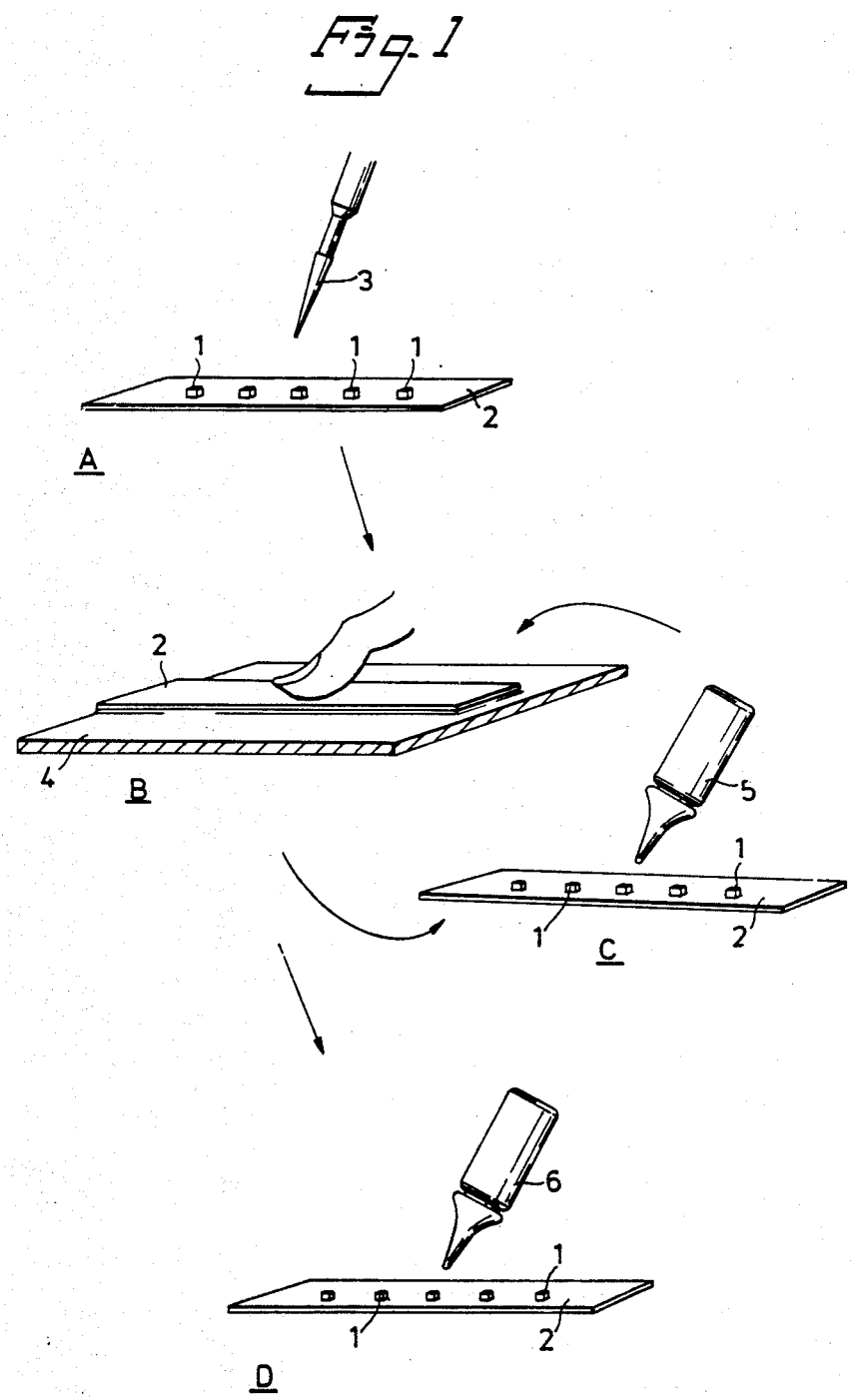

United States Patent [19]

Axén et al.

[11] Patent Number: 4,708,932

[45] Date of Patent: Nov. 24, 1987

[54] METHOD AND DEVICE FOR BIOSPECIFIC AFFINITY REACTIONS

[75] Inventors: Rolf E. Axén, Bälinge; Göran L. Kaj, Upsala; Rune Björkman, Bälinge, all of Sweden

[73] Assignee: Pharmacia AB, Upsala

[21] Appl. No.: 656,976

[22] PCT Filed: Feb. 2, 1984

[86] PCT No.: PCT/SE84/00033

§ 371 Date: Sep. 28, 1984

§ 102(e) Date: Sep. 28, 1984

[87] PCT Pub. No.: WO84/03150

PCT Pub. Date: Aug. 16, 1984

[30] Foreign Application Priority Data

Feb. 2, 1983 [SE] Sweden ................................. 8300553

[51] Int. Cl.$^4$ ...................... G01N 33/52; G01N 33/53; G01N 33/544; C12N 11/04
[52] U.S. Cl. ........................................ 435/7; 422/69; 435/174; 435/177; 435/179; 435/180; 435/181; 435/182; 435/805; 436/528; 436/529; 436/530; 436/531; 436/535; 436/541; 436/807
[58] Field of Search ................. 424/3, 1.1; 422/56–61, 422/69, 71; 435/4, 5, 6, 7, 174, 177, 179, 180, 181, 182; 436/524–533, 541, 535

[56] References Cited

U.S. PATENT DOCUMENTS

| 3,376,114 | 4/1968 | Eberle | 436/500 |
| 3,770,383 | 11/1973 | Price | 436/527 |
| 3,951,748 | 4/1976 | Devlin | 195/103.5 R |
| 4,116,638 | 9/1978 | Kenoff | 436/527 |
| 4,278,651 | 7/1981 | Hales et al. | 424/1 |
| 4,293,536 | 10/1981 | Jensen et al. | 424/1 |
| 4,540,660 | 9/1985 | Harte et al. | 436/535 |

FOREIGN PATENT DOCUMENTS 0013156 9/1980 European Pat. Off. .
0051183 12/1982 European Pat. Off. .
1392912 5/1975 Netherlands .

Primary Examiner—Christine M. Nucker
Attorney, Agent, or Firm—Fred Philpitt

[57] ABSTRACT

An improved process of performing analysis methods based upon biospecific affinity reactions in heterogeneous systems, wherein a ligand dissolved in a liquid is reacted with a receptor immobilized on a carrier, characterized by utilizing as the carrier a porous matrix in the form of a material body having an open capillary pore system capable of absorbing and retaining liquid phase and having such limited void dimensions that the total reaction rate of the biospecific reaction or reactions within the pore system between ligand and immobilized receptor will be at least substantially independent of the diffusion of the ligand in the liquid phase. A porous matrix for use in said process has the characteristics mentioned above.

13 Claims, 5 Drawing Figures

METHOD AND DEVICE FOR BIOSPECIFIC AFFINITY REACTIONS

The present invention relates to an improved and simplified method of performing analytical determination methods based upon biospecific reactions in heterogeneous systems, as well as a matrix to be used therefor.

A great number of biochemical determination methods are based upon biospecific affinity reactions between a receptor and a ligand. As examples of antigen och antibody, enzymatic determination methods, such as enzyme-substrate or enzyme-co-enzyme, lectin-sugar, etc. Usually the ligand is the component to be determined and is dissolved in a liquid, while the receptor is immobilized on a carrier in contact with the liquid. By making a known quantity of a ligand labelled with a detectable group, or a so-called marker, compete with the non-labelled ligand or, alternatively, adding an excess of labelled ligand to the carrier after the reaction with the non-labelled ligand, the content of non-labelled ligand may be determined.

In, for example, radio-immunoassay or the so-called RIA-technique radioactive isotopes are used as markers. In this technique, for example, antigen molecules in a sample are caused to compete with added isotope-labelled antigen molecules for the available sites on antibodies bound to a carrier. After the reaction non-bound material is removed by washing, and the amount of remaining radioactivity on the carrier indicates the concentration of antigen in the sample. Alternatively, in accordance with the above, the antigen sample may be added to the carrier before the addition of the isotope-labelled antigen is added.

As carriers small spheres of gels or cellulose, small paper discs or simply the inside of a test-tube have been used. The actual biospecific reactions in question, however, proceed relatively rapidly, and in the heterogeneous reaction systems obtained with the above mentioned carrier types the transport phenomenons in the solution will therefore be determining for the total reaction rate and thereby the time it takes for the reaction to be completed to such an extent that a measurement may be made. In the free liquid volume there is a transport, i.e. an equalization of concentration differences, through convection, while at the interface there is always an adsorbed liquid layer through which the transport is effected only through diffusion. The thickness of this reaction rate determining diffusion layer may be reduced by agitation, and stirring or vibration of the reaction system is therefore used to reduce the diffusion dependence. Another method used to increase reaction rate is to enlarge the surface area of the carrier. Thus, e.g., a substantial independence of diffusion has been achieved without agitation by forming the carrier as micro-sized gel particles.

These methods for reducing the diffusion dependence are, however, associated with disadvantages. Thus, the use of agitation requires special apparatus and the reproductibility will not always be satisfactory due to the difficulty of maintaining constant agitation conditions. If, on the other hand, the material transfer rate is increased by surface enlargement of the carrier, as, e.g., for the above mentioned microgel particles, the separation and wash steps will instead be more complicated. In addition centrifugation is necessary to separate the liquid phase from the carrier.

The present invention relates to a new method of optimizing the rate of biospecific affinity reactions in a heterogeneous system, which method at the same time provides a more simplified and more reliable analysis procedure without the use of neither agitation nor centrifugation. The invention is based upon a combination of surface area enlargement and reduction of the thickness of tChe diffusion layer, namely upon the concept that all the reactions are carried out completely within an open-pored, liquid-absorbing matrix body, in the pores of which the receptor is immobilized and which has limited void dimensions selected such that the distance between the solid phase surfaces thereof confines the diffusion layer to such an extent that the reaction rate of the reactant or reactants in question will be at least substantially independent of the diffusion rate of the dissolved component or ligand that is to react with the matrix-bound receptor.

The matrix body forms a "self-contained room" which due to its porosity will have a great surface area capacity. It may therefore be given relatively small dimensions and is preferably supported on a suitable holder, and special reaction vessels are therefore not necessary. The various liquid sin the analysis may readily be added, e.g., by dripping with a pipette or the like, and be removed, e.g., by squeezing of a resilient matrix material or aspirated with an aspirator, pipette or in any other suitable manner.

Performing the reaction within a porous matrix body according to the invention gives a better reproductibility and a more rapid analysis procedure than the conventional methods and will not require any special apparatus other than in certain cases for the determination of the marker. The method of the invention may therefore in some variants thereof be performed with very simple means, e.g., in a conventional doctor's practice, as will be described further below.

To perform biospecific affinity reactions in porous matrixes, as according to the invention, is per se known in the prior art. For example, the British patent specification 1,420,916 discloses a reaction cell for use in biospecific reactions, such as a radio-immunoassay reaction, which reaction cell includes a matrix pad of a porous absorbent material supported on a support provided with holes. One reaction component may be provided within the matrix, e.g., in freeze-dried form, and the other reaction component added in the actual test, the particulate reaction products formed being retained in the matrix. The purpose of performing the reactions in a porous matrix according to the British patent specification is, however, primarily to avoid the reagent losses obtained in conventional methods by splashes and wetting of the reaction vessel above the liquid level. Thus, in the above patent specification the possibility of accelerating and optimizing the reaction rate of the analysis reactions in the matrix by making it independent of the diffusion rates of the dissolved components, as according to the present invention, has neither been sought for nor realized. This also applies to the methods and devices of numerous other publications, for example, EP-A-13156, SE-B-407114, U.S. Pat. No. 3,951,748 and EP-A-51183. Such a diffusion independence indeed puts special requirements on the pore size and geometry of the matrix which there has been no reason to define in the prior art, the particular problem and even less its solution through the present invention not having been realized.

Hereinafter a simplified theorectical discussion of the problematic nature of the method of the invention will follow. According to a theoretical way of regarding it, there is in a heterogeneous system formed a layer of a defined thickness, in which the transport is effected only by diffusion, the so-called Nernst diffusion layer, whereas the solution outside this layer is completely mixed by convection. As mentioned above the thickness of the layer may be reduced by agitation, but also in case of vigorous agitation a diffusion layer remains which has a thickness of the order of 10–100 μm.

It is well-known that for a plane diffusion layer having the thickness L the following relationship is applicable to the concentration of the diffusing species in the layer in steady state and if there is no supply or removal of diffusing substance between the plane limiting surfaces of the diffusion layer:

$$c(x) = \frac{C_L - C_0}{L} \cdot x + C_0 \quad (1)$$

wherein x is the longitudinal coordinate normal to the limiting surfaces, $C_0$ is the concentration at x=0 (i.e. one surface section of the layer) and $C_L$ is the concentration at x=L.

There is thus formed a linear concentration gradient having the slope $$\frac{\partial c}{\partial x} = \frac{C_L - C_0}{L} \quad (2)$$

and the total flow through the diffusion layer is therefore given by the expression $$-\frac{\partial Q}{\partial t} = A \cdot D \cdot \frac{Q}{V \cdot d} \quad (3)$$

wherein Q is the quantity of the dissolved component in the free liquid volume V, d is the thickness of the diffusion layer, D is the diffusion constant and A is the area of the solid phase. (The above mentioned equations 1–3 may easily be derived starting from Fick's first and second laws.)

Since all the parameters except Q are constant, Q will vary exponentially with time. In order that the system should not be diffusion-limited, the half-lift of the diffusion process should be less than the half-life of the chemical reaction (which is assumed to follow first order kinetics as far as the dissolved component is concerned). The half-life of the diffusion process may thus be reduced by making A large and/or making d small.

In a capillary (being the simplest special case of the pores of the matrix of the invention) the diffusion must, however, be considered as taking place between two concentric cylindrical surfaces instead of plane surfaces, and the expression (1) is then replaced by:

$$c(r) = \frac{C_L - C_0}{\ln(r_L/r_0)} \cdot \ln(r) + K \quad (4)$$

wherein $r_0$ is the radius of the outer cylinder surface, $r_L$ is the radius of the inner cylinder surface and K is a constant. As distinguished from the case of a plane diffusion layer no linear concentration gradient will thus be obtained in this case but $$\frac{\partial c}{\partial r} = \frac{C_L - C_0}{r \cdot \ln(r_L/r_0)} \quad (5)$$

For the special case that the radius of the inner cylinder surface is 1/e(~0,37) of the outer one the expression (5) will, however, be simplified to $$\frac{\partial c}{\partial r} = \frac{C_L - C_0}{r} \quad (6)$$

For a system in which the solid phase consists of the wall of a capillary having the radius $r_0$, the concentration of the dissolved phase is assumed to be independent of the radius for r<0,37. $r_0$ and to be zero for r=$r_0$, and a stationary gradient is maintained therebetween, the following relationship analogous to the expression (3) may be set up:

$$-\frac{\partial Q}{\partial t} = A \cdot D \cdot \frac{Q}{V \cdot r_0} \quad (7)$$

Here the radius of the capillary corresponds to the diffusion layer d. In the same way as for equation (3) above the half-life of the diffusion process may be reduced by increasing A and/or reducing d. As mentioned d may be reduced in conventional manner by agitation, or in accordance with the present invention by limiting the physical dimensions of the system. The diffusion layer of the capillary can thus never be greater than half the capillary diameter.

This capillary model may be applied to a porous matrix of the invention, the capillary radius then corresponding tot he pore radius. For the reaction systems and concentration ranges concerned here the half-life of the chemical reaction may be assumed to be of the order of 1–10 minutes, and the diffusion constants range form $10^{-7}$–$10^{-6}$ cm$^2$/s. The insertion of these values into equation (7) will for an effective solid phase area of 20 cm$^2$/100 μl of liquid volume give a maximum value for d (or $r_0$) of approximately 100 μm for a diffusion independence to be achieved.

The effective size of the solid phase surface will depend on d. To the extent that surface area enlarging elements of a magnitude less than d are present, they will not contribute to the effective surface A since no increase of the interface between the diffusion layer and the free liquid volume will result.

The above mentioned value of about 100 μm diameter for the special case of cylindrical capillary pores may thus be taken as an approximate guiding value of the maximal pore diameter of a matrix of the invention having cylindrical pores for diffusion independence to be achieved under the indicated conditions. Of course, the pore configuration of the matrix may, within the scope of the invention, vary substantially from the discussed cylindrical configuration, and the size/configuration requirements on the pores may therefore be stated as being such that the resulting diffusion process in the matrix pores should be substantially equivalent to that obtained in cylindrical capillary pores having the specified diameter/area/volume dimensions.

Although a certain deviation from the ideal maximum size of the pores may occur without any essential practical influence on the result, the matrix material should be relatively homogeneous. There should thus not be any larger cavities or vacuols which may be filled with liquid and give rise to comparatively thick diffusion layers between the component dissolved in the liquid and the component immobilized to the matrix skeleton. Moreover, the matrix skeleton should neither-at least not to any greater extent-be permeable or exhibit porosity and thereby produce undefinable diffusion layers. There is, of course, a lower limit of the pore sizes for the preparation of the matrix with the immobilized component not to be prevented. This is, however, easily realized by every person skilled in the art and need therefore not be discussed any further herein.

Suitable pore dimensions and the necessary homogeniety of a certain matrix material may relatively simply be determined empirically by the person skilled in the art, e.g. by comparing the reaction rates in matrix materials of different pore dimensions with the reaction rate in a conventional heterogeneous system, wherein the diffusion dependence is substantially eliminated by stirring or vibration, or with a corresponding surface area enlarged system, such as, e.g., the above mentioned microgel particles.

The above mentioned porosity requirements being met, the matrix will obtain such a capillary that the liquid samples, wash solutions etc. can be immediately absorbed and retained by the matrix body. Since the liquid medium in the biospecific affinity reactions in question usually is water, the pore surfaces of the matrix material should be hydrophilic for the liquid to be absorbed and retained by the matrix. Hydrophilic absorption surfaces of an otherwise hydrophobic material may be obtained by treatment with surface-active agents or by lasting surface treatment with known techniques, as will be discussed below. Possibly a hydrophobic pore surface will be sufficiently hydrophilic when the immobilized component or receptor is applied into the matrix.

The matrix material may be hard or soft. A soft matrix may be preferable in certain embodiments, as will be further discussed below. The necessary porosity for the purposes of the invention may be achieved in, for example, sintered, fibrous or spongy materials. The matrix material may be selected among a variety of materials, and as examples may be mentioned glass, metals, various plastics, such as polyurethanes, polyvinyl alcohols, polyethylenes, nylons, and certain natural sponges, textile materials, etc. Advantageously, however, the matrix material is selected from a soluble or insoluble polysaccharide, a derivate thereof or a polysaccharide coated synthetic material. Examples of polysaccharides that may be used are cellulose, dextran, agarose, starch, etc., which optionally may be derivatized, e.g., cross-linked to increase the adhesitivity or to reduce the solubility thereof. A particularly suitable material is a cellulose foam having a water absorption capacity in the range 7-20 times the dry weight thereof or corresponding other polysaccharide foams having similar properties. Among the cellulose foams particularly those marketed under the trade names Wettex ® and Sugi ® may be mentioned. Wettex ® is a registered trade mark for a cellulose foam produce marketed by Celloplast AB, Norrköping, Sweden which in dry state has a water absorption capacity of about 10-15 times its dry weight. Sugi ® is a registered trade mark for a similar product marketed by Kettenbach Dental, Eschenburg, West-Germany.

The immobilized component or receptor may be bound to the matrix by covalent bonds or by adsorption. In this connection the so-called CNBr-method, e.g. as disclosed in U.S. Pat. No. 3,645,852 (the disclosure of which is incorporated by reference herein), has proved to give very great advantages. Optionally the surfaces of the cavities or voids may be modified to improve their properties towards the ligand or ligands to be used, e.g., to prevent non-specific binding of the components in the liquid phase to the matrix skeleton. Various techniques for the coating of surfaces of solid bodies or substrates, including the above materials, with, for example, gel or polymer layers are well-known in the art. A new advantageous surface coating method is described in our European patent application No. 83850274.8 (the disclosure of which is incorporated by reference herein), which relates to the surface coating with a polymer layer, the crosslinking degree of which may be controlled depthwise, for example, such that the cross-linking degree decreases from the substrate and outwards. This is accomplished by absorbing, e.g., CNBr in a synthetic porous polymer body, and subsequently immersing it in a polysaccharide solution (e.g. agarose) having a suitable pH. The pores of the body will then be coated by an anisotropic CNBr-cross-linked agarose layer to which components may be immobilized.

Despite the fact that the conditions for avoiding diffusion-limited kinetics in accordance with the above have been met, there may, if the solid phase consists of or has been provided with a gel or polymer layer wherein one reaction component has been immobilized, be formed an "inner" concentration gradient of the dissolved component during the reaction causing a lowered apparent concentration of the immobilized component. A satisfactory high apparent concentration (greater than 80% of the true concentration) will be obtained if the well-known Thiele's module, $\omega$, for the system is less than 2. This gives $$\omega = \frac{z}{3} \cdot \sqrt{\frac{\ln (2)}{t_{\frac{1}{2}} \cdot \overline{D}}} \qquad (8)$$

wherein z is the thickness of the gel layer $\bar{t}_\alpha$ is the half-life of the reaction in the gel layer and $\overline{D}$ is the diffusion constant of the component dissolved in the gel layer. If $\overline{D}$ is set equal to D and $\bar{t}_\alpha$ is set to one hundredth of the previously assumed half-life of the whole system the requirement that $\omega < 2$ if $z < 15$ μm will be met. Thus, a gel or polymer layer having a thickness lower than about 15 μm may be considered as lacking importance for the total reaction rate.

A matrix body for use in the invention may be made in any suitable form, e.g. in the form of cubes, blocks, balls, spheres, etc. For the purposes of the invention the matrix body is suitably mounted to a holder, e.g. by blueing to a plate, fixing in a frame or in the wells of a plate.

The receptor components are suitably immobilized to the matrix material before it is cut or otherwise formed into individual smaller matrix bodies. Of course, the application of the receptor component or components may also be performed in the preformed matrix body.

As examples of biospecific reactions, for which the method and the matrix body of the invention may be used, immunological reactions, such as the reaction between antigen or hapten and antibody, enzyme reactions, such as enzyme-substrate or enzyme-co-enzyme, lectin-sugar, protein A-Fc-part of IgG, biotin-avidin, neurotransmitter/receptor reactions, such as acetyl choline-acetyl choline-receptor etc. may be mentioned.

Concerning the immunological reactions particularly the use of monoclonal antibodies as the receptor or ligand in the present analysis method should be mentioned.

Among the various analysis methods that may be contemplated radioimmunoassay (RIA) and enzyme immunoassay (ELISA), wherein radioactively labelled groups or enzymes, respectively, are used as the detectable groups or markers, may be mentioned. Also methods based upon fluorescent or phosphorescent markers, markers showing chemiluminiscense, etc may be mentioned.

The analysis methods may be in conventional manner be carried out such that the marker will compete with the ligand to be detected, or according to the sandwich model such that first the sample is added and then an excess of labelled antibody. Among other techniques the double antibody method (DASP) and RAST (radio allergosorbent test) may be mentioned.

As mentioned above the method of the invention results in a considerably more rapid and simplified procedure in comparison with the previously used methods since the matrix body forms a self-contained room having a large surface capacity, wherein the liquid added may reproducibly be absorbed and retained and wherein the biospecific affinity reactions proceed with an optimal rate, diffusion-limited kinetics being avoided. In certain types of analysis, such as, e.g., the above mentioned RIA or ELISA, where the sample is added to the matrix before the isotope or enzyme labelled ligand is added, essentially the whole absorbing capacity of the matrix body must be utilized. In such a case a slight deficit in relation to the maximum volume absorbable by the matrix is suitably added. In the corresponding test methods in which the sample and marker substance compete for available reactive sites the whole matrix volume need not be utilized. Suitable liquid volumes for practical use are, e.g., from about 10 µl to about 1 ml.

In the analysis methods to which the method and matrix body of the invention may be applied the measurement with regard to the marker may in conventional manner (after the liquid has been separated from the matrix) be performed either on the matrix body or on the separated liquid phase according to the method of analysis in question.

The method of the invention permits the development of very simple determination systems, particularly in analysis methods based upon a colour marker. Thus, the measurement may in conventional manner be performed directly on the matrix surface by means of reflection photometry. For measurement on the separated liquid phase a special holder for the matrix body may be designed which in the lower part thereof is provided with a small container having a volume which is at least somewhat greater than the maximum liquid volume that can be absorbed in the matrix body. If the matrix material has a low hydrophilicity the liquid volume retained in the pores may be completely displaced into the container by means of a hydrophobic liquid, e.g. heptane. A measurement with regard to the colour intensity of the displaced liquid in the container below the matrix body may then be effected photometrically in conventional manner.

An alternative colour detecting system consists in, after the reaction of the marker in the matrix body, applying thereto a second matrix body having a smaller pore size than the first matrix body to draw liquid phase over to the second matrix, which may contain a substrate for the colour reaction.

In the following a simple embodiment of the test method of the invention will be described with reference to the accompanying drawings, in which FIGS. 1A thru 1D are sequential perspective views illustrating a series of steps that are involved in the method of our invention.

In the figures matrix bodies 1 of the present invention are fixed to a plate 2. The matrix bodies 1 contain a suitable receptor coupled or adsorbed to the matrix skeleton. To perform, for example, an enzyme immunoassay (EIA) with regard to a sample containing antigen, the receptor is an antibody to this antigen. A suitable sample quantity in relation to the absorbable volume of the matrix body is added to each matrix body 1 by means of a pipette 3. After incubation for a suitable time (e.g. 10 minutes) the plate 2 is turned and pressed against an absorbing material 4, e.g. paper, such that all the liquid in the matrix bodies 1 are drawn over thereto (B). A washing solution is then supplied with a drop bottle 5 (C), whereupon the washing solution is drawn over to an absorbing material in the same way as above. This step may be repeated several times to achieve a thorough washing out. The same volume of enzyme-antibody conjugate as the sample is then pipetted directly onto the matrix bodies 1 (A), and incubation is again effected for, e.g., 10 minutes. Washing is once more performed in the same way as above (C), and then the substrate upon which the enzyme marker is to act is added using a drop bottle 6 (D). After about 5 to 10 minutes the results may be read visually.

The above described device for performing the invention is, of course, only an example thereof, and obviously many other devices based upon the principle of the invention may be used.

In the following the invention will be illustrated by some non-limiting examples.

EXAMPLE 1

This example describes the use of a spongy microporous cellulose material as the solid phase in a sandwich enzyme immunoassay for semiquantitation of Streptococcus A antigen.

Coupling of antibodies

Square pieces (5×5 mm) were cut out from Wettrex ® cloth (Wettex ® is a registered trade mark for a white spongy cellulose foam material prepared from viscose and which in dry state has a thickness of about 2-4 mm, a grammage of about 250-350 g/m$^2$ and a water absorption capacity of about 10-15 times its dry weight; marketed by Celloplast AB, Norrkoping, Sweden) by means of a pair of scissors. One hundred such pieces were then washed with 0.1N HCl, distilled water, 0.1M NaOH and distilled water, respectively. Thereupon the supernatant was completely removed by aspiration and 20 ml of 0.6M phosphate buffer (pH 11.7) were added. For activation of the cellulose material the reaction vessel wasa placed in an ice-bath. The activation was initiated by the addition of 20 ml of 1% CNBr-solution in distilled water and continued for exactly 6 minutes with slow stirring, using a glass rod. Hereafter the Wettex ® pieces were carefully washed with distrilled water on a glass-filter funnel. Then the pieces were dried by acetone treatment and evaporation of the acetone at room temperature. The activated Wettex ® pieces were stored in a desiccator at +4° C. until they were coupled with antibodies.

Antibodies (gamma-globulin fraction) were diluted 100 times in 0.1M NaHCO$_3$ according to an antibody dilution curve. 30 ml were added to 100 pieces of CNBr-activated Wettex ®. The coupling reaction was allowed to continue over night at +4° C. and with no shaking. The Wettex ® pieces were then in turn carefully washed with 0.1M NaHCO$_3$, 0.1M Tris. HCl, pH 8.0, and washing buffer (0.3M NaCl, 0.1% Tween ®20, 0.01% NaN$_3$ in 0.1M phosphate buffer, pH 7.4).

In an analogous manner antibodies were coupled to conventional paper discs.

Uptake of antigen

Figure 2:
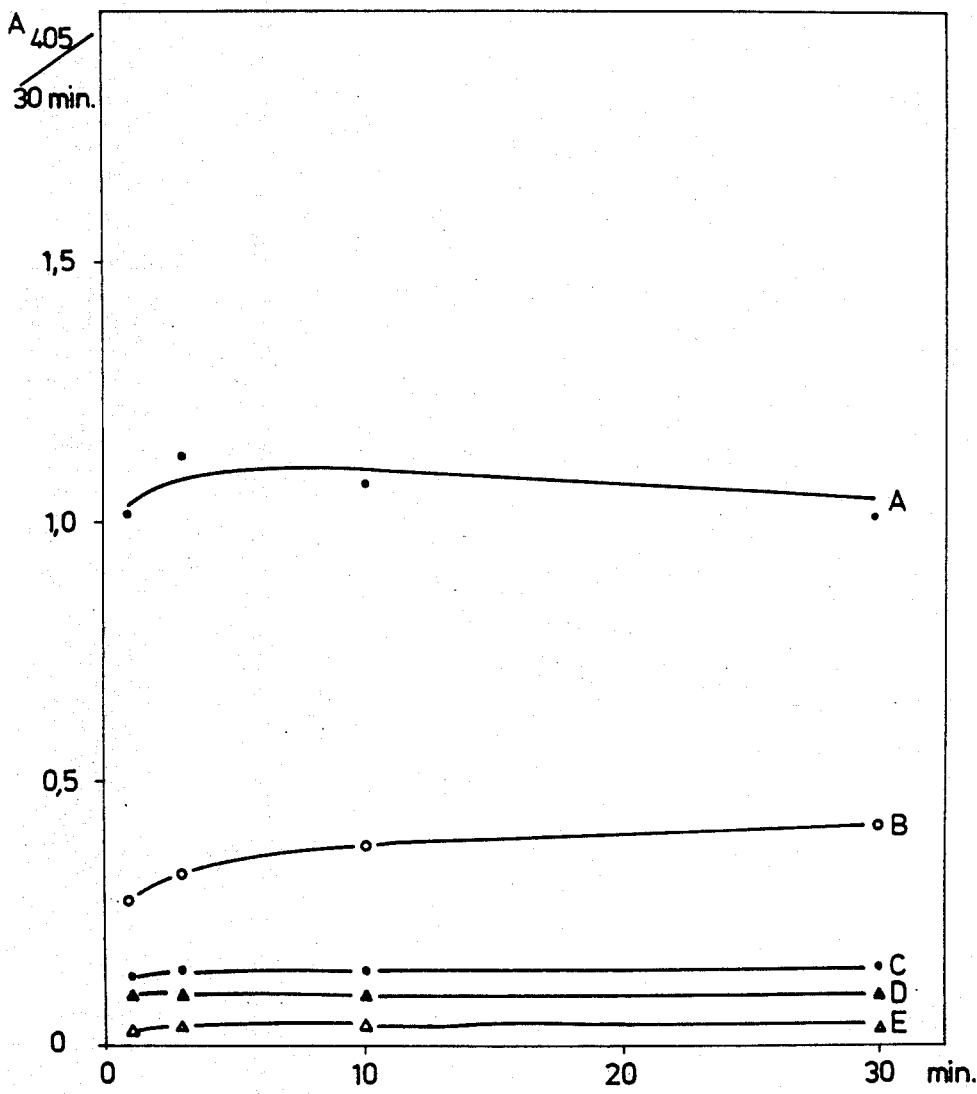

Two different concentrations of the polysaccharide antigen from Streptococcus A, extracted from $10^8$ bacteria/ml and $10^6$ bacteria/ml, respectively, were used. The above mentioned washing buffer and Wettex ® pieces were used as negative controls. Samples of 100 μl were added both to the Wettex ® pieces and paper discs with antibodies covalently coupled as above and incubated for 1, 3, 10 and 30 minutes. Hereafter the supports were washed with the washing buffer, and 100 μl of an enzyme-antibody conjugate of galactosidase bound to antibodies against Streptococcus A antigen (the conjugate is commercially available from Pharmacia AB, Sweden) diluted to 2.4 μg of antibody/ml were added and incubated for one hour, whereupon the supports were washed once again as above. The supernatant was removed by aspiration, and 200 μl of o-nitrophenyl-β-galactoside was added as the enzyme substrate. After 30 minutes the enzyme reaction was stopped with 500 μl of 0.5M Na$_2$CO$_3$. the supernatant was transferred to disposable polystyrene cuvettes, and the colour was measured at 405 nm in an automatic filter photometer (LKB 7400 Ultralab system). The results are presented in FIG. 2, where the curves A and C show the uptake for the Wettex ® support at the antigen concentrations of $10^8$ and $10^6$, respectively, bacteria/ml, curve B is the uptake for paper discs at $10^8$ bacteria/ml, curve D is the control with Wettex ® pieces, and curve E is the control with paper discs.

From this Figure it appears that the reaction rate with Wettex ® as the support for the antibodies was much higher than that with the paper discs, and that a plateu level (equilibrium) was reached within a few minutes both with a high and a low concentration of antigen.

Determination of the detection limit

To determine the detection limit of this EIA-system a standard curve with serially diluted Streptococcus antigen was set up. The concentrations of bacteria of the extracts varied from $10^8$/ml to $10^4$/ml. 100 μl of each dilution was incubated with the Wettex ® pieces with coupled antibodies for 15 minutes. Then the pieces were washed as above and 100 μl of the above enzyme-antibody conjugate, diluted 100 times with the same buffer as used above, was incubated with the Wettex ® pieces for another 15 minutes. After the last washing step the enzyme activity was determined in the same manner as above. From the obtained standard curve it was found possible to quantitate bacteria contents down to $10^5$ bacteria/ml with this rapid immunoassay.

Test method

Wettex ® pieces with coupled antibodies as above were then used to illustrate the test method with the device therefore as described previously with reference to FIG. 1. Almost dry Wettex ® pieces with coupled antibodies (the water was aspirated) were placed on a plastic slide (2 in FIG. 1), upon which glue (RX glue, Casco AB, Sweden) had been applied at the fixing sites for the Wettex ® pieces. After 15 minutes the pieces had been fixed to the slide, 50 μl of antigen sample were then applied directly to the Wettex ® pieces. All liquid was absorbed, and after 10 minutes incubation the slides were turned and the Wettex ® pieces pressed against filter papers, whereupon the washing solution (the same buffer as above) was added with a drop bottle. The washing solution was pressed out of the Wettex ® pieces in the same way as above, and this washing procedure, which only required very samll quantities of washing solution, was repeated three times. Then 50 μl of the above used enzyme-antibody conjugate was added and incubated for another 10 minutes. The washing procedure was then repeated, and finally the Wettex ® pieces were wetted with the above mentioned o-nitrophenyl-β-galactoside substrate. The results could subsequently be read visually within 5-10 minutes. By stopping the reaction with 0.4M carbonate buffer, pH 9.0, containing 25% ethylene glycole, it was possible to maintain the positive reaction stable for several hours.

EXAMPLE 2

In this example the uptake of antigen for a porous polymer of the invention is compared with that of a dense polymer, the antibodies being coupled to an agarose layer applied to the respective polymer.

Coating with the agarose layer 27 mg of agarose in 10 ml of water were heated under stirring on a boiling water bath until the agarose melted. The solution was then allowed to cool over night. Hereafter 2.5 ml of a 12.5M sodium hydroxide solution were added and the mixture was vigorously stirred for 1 hour.

$5 \times 5$ mm square discs of 1 mm thick Plexiglas ® and cylindrical plugs of 5 mm diameter, stamped out of a 6 mm thick porous string of polyvinyl acetate (Electrode strip, Pharmacia AB, Sweden), respectively, were introduced into a glass tube provided with a tight stopper and containing crystals of cynaogen bromide. After 1 hour the discs and plugs, respectively, were taken out and incubated for 2 hours in 500 μl each of the above prepared agarose solution. The solution was aspirated, the discs and plugs, respectively, washed repeatedly with a 0.5M sodium bicarbonate solution and stored for 24 hours in this solution.

Coupling of antibodies

The discs and plugs, respectively, were transferred into a beaker immersed in an ice bath and containing 4 ml of 0.5M potassium phosphate solution at pH 11.5 and 1 ml of a solution of 1 g cyanogen bromide in 9 ml of water. The discs and plugs, respectively, were each transferred into tubes containing 200 μl of antiserum against rabbit-IgG (Miles Laboratories Ltd., England) from sheep precipitated with 18% sodium sulphate solution, dissolved to the origina volume in 0.15M sodium chloride solution and diluted 50 times in 0.1M sodium bicarbonate solution containing 0.1% Tween ®20. After incubation at +4° C. over night the solution was aspirated, and the discs and plugs, respectively, were washed $3 \times 10$ minutes with 0.5M sodium bicarbonate solution containing 0.1% Tween ®20, 4 hours with 0.1M ethanolamine solution, being 0.1M with regard to sodium phosphate, pH 8, and 5×30 minutes with 0.1M sodium phosphate solution, being 0.15M with regard to sodium chloride and containing 0.5% Tween ®20, pH 7.4.

Preparation of rabbit-IgG-125-I

A reaction tube of glass was placed on an ice bath. To the tube 50 μl of rabbit-IgG (Miles Laboratories Ltd.) 1 mg/ml in 0.2M sodium phosphate, pH 7.0, 100 μl of 1.5 mM chloramine T (Merck, pro analysi) and 0.72 μl of Na-125-I, 500 mCi/ml (New England Nuclear, USA) were added. After 2 minutes the reaction was stopped by the addition of 20 μl of 0.1M sodium thiosulphate solution and 50 μl of 0.1M potassium iodide solution. The reaction mixture was desalted on a column containing Sephadex ® G-25 (Pharmacia AB, Sweden) which had been equilibrated with 0.05M sodium phosphate solution, being 0.05M with regard to sodium thiosulphate and containing 0.05% Tween ®20 and 2% human serum albumin (Sigma, USA), pH 7.4. The void fraction was diluted 4 times with 0.1M sodium sulphate solution containing 0.1% Tween ®20, pH 7.5.

Uptake of antigen

To 10 ml of 0.1M sodium phosphate solution of pH 8 and containing 0.1% Tween ®20 10 μl of a solution containing 10 μg/ml of rabbit-IgG-125-I, prepared as above, were added. The agarose-coated discs and plugs, respectively, were incubated for 1 minute, 3 minutes, 15 minutes, 1 hour and 5 hours, respectively, each in 200 μl of this solution. The discs and plugs, respectively, were then washed with 0.3M sodium chloride solution containing 0.5% Tween ®20, and the remaining radioactivity was measured. The measured activity in % of the totally added activity is indicated in the following Table.

TABLE 1

| Time | % of total activity added | |
|---|---|---|
| | Disc | Porous plug |
| 1 min | 3 | 17 |
| 3 min | 6 | 26 |
| 15 min | 14 | 39 |
| 1 h | 30 | 58 |
| 5 h | 59 | 68 |

From the Table above it appears that the uptake of antigen and thereby the flattening out of the reaction curve (which indicates substantially completed reaction) occurs considerably more rapidly for the porous plugs than for the discs. The use of such porous plugs in biological tests based on biospecific affinity reactions thus requires substantially shorter incubation periods than the corresponding test performed on dense carrier substrates.

EXAMPLE 3 hGH-assay

Microporous discs (Wettex ®, Celloplast AB, Norrköping, Sweden) having a diameter of 6.2 mm were activated with 1% BrCN-solution. To each disc 5 μg of sheep anti-hGH-antibodies (prepared from sheep antiserum by Na₂SO₄- precipitation) were coupled. The prepared discs were kept in a 0.05M Na-phosphate buffer containing 0.9% NaCl, 0.3% Dextran T40 (Pharmacia AB, Sweden) and 0.05% NaN₃, pH 7.4, at +4° C.

Before performing the hGH-assay the surplus buffer was removed from the discs by means of a nozzle connected to a water aspirator. To each test-tube one Wettex ®-disc and 100 μl of various dilutions of purified hGH (0.5–150 μU/l) in hGH-free horse serum [hGH-free diluent, Phadebas hGH PRIST ®, (Pharmacia AB, Sweden)] were added. The test-tubes were incubated for 15 minutes at 23° C. whereupon the microporous discs were washed by adding 5×250 μl of sline to each disc with aspiration between the additions.

100 μl of $^{125}$I-anti-hGH-solution (IgG-antibodies raised in rabbits, Phadebas hGH-PRIST ®, 9 ng/test-tube) were added to each test-tube before they were incubated for 2 hours at +23° C. The discs were then washed as above, after which the radioactivity was measured by a gamma-counter. The results are presented in Table 2 below.

TABLE 2

| Conc. of hGH μU/l | Measured radioactivity cpm | % Bound of total radioactivity added |
|---|---|---|
| 0 | 186 | 0.9 |
| 0.5 | 785 | 4.0 |
| 1.5 | 1086 | 5.5 |
| 5 | 2604 | 13.2 |
| 15 | 4929 | 25.0 |
| 50 | 7093 | 36.0 |
| 150 | 9063 | 46.0 |
| 300 | 10248 | 52.0 |

To obtain similar results with anti-hGH-antibodies coupled to a BrCN-activated paper disc (Phadebas hGH-PRIST ®, Pharmacia AB, Sweden) the first incubation takes 3 hours at +23° C., while about 16 hours are needed at the same temperature for the second incubation. Thus, by using this microporous matrix instead of a paper disc, the incubation time may be decreased considerably, resulting in a total test time of less than 3 hours compared with 20 hours with the conventional PRIST-method with paper discs.

EXAMPLE 4

Insulin-assay

Microporous discs (Wettex ®, Celloplast AB, Norrköping, Sweden) having a diameter of 6.2 mm were activated with 1% BrCN-solution. To each disc 5 μg of anti-guinea-pig-IgG-antibodies (prepared from sheep by Na₂SO₄-precipitation) were coupled. After washing, which included ethanolamine treatment, the discs were kept in a 0.05M Na-phosphate buffer containing 0.9% NaCl, 0.3% Dextran T40 (Pharmacia AB, Sweden) and 0.05% NaN₃, pH 7.4, at +4° C.

To the test tubes the following reagents were added:
25 μl of various dilutions of human insulin in phosphate buffer of pH 6.5 (0.1M Na-phosphate with 1% human serum albumin and 0.05% NaN₃),
50 μl $^{125}$I-insulin (Phadebas ®-insulin test, Pharmacia AB, Sweden, about 40 pg/tube),
25 μl of guinea-pig-anti-insulin antiserum diluted in a phosphate buffer of pH 7.4 (0.05M Na-phosphate, 0.9% NaCl, 0.3% human serum albumin, 0.05% NaN₃).

The test-tubes were incubated for 1 hour at +23° C. before one antiguinea-pig IgG-disc as above was added to each test-tube. Before this addition the suplus buffer was removed from the discs by means of a nozzle connected to a water aspirator. Incubation was performed at +23° C. for 1.5 hours. The discs were then washed with 5×250 μl of saline with 0.05% Renex 30 (polyoxyethylene ether; Atlas Chemie, Essen, West-Germany). Each addition of saline was followed by an immediate aspiration of the liquid. The radioactivity of the test-tubes were measured with a gamma-counter. The results of the analysis are presented in the following Table 3.

TABLE 3

| Conc. of insulin $\mu$U/ml | Measured radioactivity cpm | % Bound of zero sample |
| --- | --- | --- |
| 0 | 1887 | 100 |
| 3 | 1747 | 92.6 |
| 10 | 1453 | 77.0 |
| 30 | 1123 | 59.5 |
| 100 | 623 | 33.0 |
| 240 | 482 | 25.5 |
| 1000 | 340 | 18.0 |
| Total activity added | 4259 | |

As appears from the above a competitive immunoassay may be performed in a liquid phase with a short incubation time without agitation and with a fast and convenient separation step for bound and free tracer, where no centrifuge or other sophisticated equipment is needed.

EXAMPLE 5

In this example a microporous carrier matrix of the invention is compared reaction-kinetically with macro-spheres and micro-spheres with regard to the uptake of antigen as a function of time.

Activation and coupling of antibody

Macro-spheres 0.5 g of agarose in bead-form, diamter 45–165 $\mu$m, (Sepharose®-6B, Pharmacia AB, Sweden) were washed with water on a glass-filter G3 and transferred into an ice-cooled beaker, 4 ml of 0.5M potassium-phosphate buffer, pH 11.5, and 1 ml of a solution of 1 g cyanogen bromide (Polysciences, Warrington, Pennsylvania, USA) in 9 ml of water were added. After 6 minutes the gel was again transferred into the glass-filter and washed with ice-cooled water. Sodium-sulphate precipitated anti-serum against rabbit-IgG (Miles Laboratories Ltd., England) from sheep was diluted to a protein concentration of 0.3 mg/ml with 0.1M sodium bicarbonate solution containing 0.1% Tween®20, and 1 ml of this solution was added to the dry-aspirated agarose gel. After careful shaking for 6 hours 2 ml of 0.2M ethanolamine in 0.1M phosphate buffer, pH 8, were added and shaking was continued over night. The gel was then washed with 0.1 M acetate buffer, pH 4, followed by 0.05M sodium-phosphate buffer, pH 7.4, containing 0.9% sodium chloride, 0.3% Dextran T 40 (Pharmacia AB, Sweden) and 0.5% Tween®20.

Micro-spheres 0.5 g of agarose in bead-form, diameter 1–3 $\mu$m, were treated as above except that the separations in the washing-steps were made by means of a centrifuge (Eppendorf 3200) instead of with a glass-filter.

Porous discs 20 micro-porous discs (Wettex®, Celloplast AB, Norrköping, Sweden) having a diameter of 4.25 mm were treated as above under "macro-sheres" except that the antibody solution contained 15 $\mu$g/ml and 2 ml thereof were charged.

Uptake of antigen as a function of time

Macro- and micro-spheres

To 200 $\mu$l of a solution of 10 mg rabbit-IgG-125-I per ml in 0.1M sodium phosphate buffer, pH 8, containing 0.1% Tween®20 2 mg of antibody-coupled agarose beads (i.e. 2 ng of rabbit IgG/6 $\mu$g protein charged in the coupling) were added. The macro- and micro-spheres were then each divided into two batches distributed on four test-tubes, one batch of which was incubated without shaking and with only slow rotation of the tubes, while the test-tubes in the other set were vigorously vibrated during the reaction period on a shaking apparatus (IKAVibrax-VXR, setting 1500, IKA-Werk, Staufen, West-Germany).

After a reaction time of 3, 15, 60 and 180 min., respectively, 1 ml of 0.3 M sodium chloride solution containing 0.1% Tween®20 were added. The gel was centrifuged down and the solution aspirated. After another washing in the same manner the radioactivity taken up by the gel was measured.

Porous discs

50 $\mu$l of rabbit-IgG-125-I solution as above were added to an antibody-coupled micro-porous disc which had been aspirated dry (i.e. 0.5 ng rabbit-IgG/1.5 $\mu$g protein charged in the coupling). After a reaction time of 3, 15, 60 and 180 min., respectively, the solution was aspirated and the disc washed twice with 0.3M sodium chloride solution containing 0.1% Tween®20. The radioactivity taken up by the disc was measured.

The results obtained are presented in Table 4 below:

TABLE 4

| | Uptake of radioactivity in percent of that totally added: | | | | |
| --- | --- | --- | --- | --- | --- |
| | Macro-spheres | | Micro-spheres | | |
| Time minutes | Without shaking | With shaking | Without shaking | With shaking | Porous disc |
| 3 | 11 | 23 | 37 | 44 | 32 |
| 15 | 16 | 54 | 60 | 52 | 63 |
| 60 | 17 | 73 | 66 | 71 | 74 |
| 180 | 21 | 77 | 72 | 77 | 86 |

From the results it appears that the improved kinetics provided by the vigorous shaking or reduction of the particle size will also be obtained by the micro-porous carrier according to the invention.

We claim:

1. In a method of performing analyses based upon biospecific reactions in heterogeneous systems, comprising the steps of
   (a) providing a self-supporting carrier matrix body capable of absorbing and retaining liquid and having a first receptor component immobilized to the pore surfaces thereof,
   (b) sampling a predetermined volume of a liquid having dissolved therein a second ligand component that is to be determined,
   (c) contacting said predetermined sample volume with the matrix bocy to be completely absorbed and retained thereby,
   (d) permitting said first and second components to react to form an immobilized complex, and
   (e) detecting, and optionally quantitating the formation of said immobilized complex in said matrix,
   (f) the improvement comprising optimizing the total reaction rate of said second component with said first component by providing said first receptor component covalently bonded to the pore surfaces of said matrix in a sufficient amount for said total reaction rate to be dependent on the diffusion of said second component in the liquid phase, and by minimizing the influence of said diffusion by selecting the pore dimensions of said matrix body so that the total diffusion process therein substantially corresponds to that of a matrix having cylindrical pores with a diameter of less than about 200 μm, but sufficiently large to permit easy passage of the reagents, to thereby make said total reaction rate substantially independent of said diffusion.

2. A method according to claim 1 wherein the pore dimensions of the carrier matrix is selected so that the total diffusion process therein corresponds to that of a matrix having cylindrical pores with a diameter of less than about 100 μm.

3. A method according to claim 1 wherein said carrier matrix body comprises a polysaccharide.

4. A method according to claim 1 wherein said carrier matrix body comprises a polysaccharide derivative.

5. A method according to claim 1 wherein said carrier matrix body comprises a cellulose material.

6. A method according to claim 1 wherein said carrier matrix body comprises agarose.

7. A method according to claim 1 wherein said carrier matrix body comprises dextran.

8. A method according to claim 1 wherein said carrier matrix body comprises startch.

9. A method according to claim 1 wherein said biospecific reaction s an immunochemical reaction.

10. A method according to claim 1 wherein the pore surfaces of the matrix body are coated with a surface-modifying layer of a different material.

11. A method according to claim 10 wherein said different material is a polymer layer.

12. A method according to claim 11 wherein the thickness of said polymer layer is less than about 15 μm.

13. A method accoridng to claim 1 whereinsaid detecting and optionally quantitating step comprises reacting said immobilized complex formed with a third component capable of reacting with said second component.

* * * * *